United States Patent [19]

Herdeman

[11] Patent Number: 4,767,557

[45] **Date of Patent: * Aug. 30, 1988**

[54] DRY BLEACH AND STABLE ENZYME GRANULAR COMPOSITION

[75] Inventor: Robert W. Herdeman, Loveland, Ohio

[73] Assignee: The Procter & Gamble Company, Cincinnati, Ohio

[ * ] Notice: The portion of the term of this patent subsequent to Nov. 17, 2004 has been disclaimed.

[21] Appl. No.: 131,294

[22] Filed: Dec. 9, 1987

Related U.S. Application Data

[63] Continuation of Ser. No. 750,569, Jun. 28, 1985, abandoned.

[51] Int. Cl.[4] ........................ C11D 3/386; C11D 3/39; C12N 9/96; C12N 9/98

[52] U.S. Cl. ........................................ 252/91; 252/95; 252/99; 252/135; 252/174; 252/174.12; 252/174.13; 252/174.14; 252/174.17; 252/174.21; 252/188.1; 252/DIG. 12; 427/213; 427/214; 427/220; 435/188

[58] Field of Search .................. 252/89.1, 95, 99, 102, 252/174.12, 174.13, 174.14, 174.17, 174.21, 91, 188.1, DIG. 12; 435/188

[56] References Cited

U.S. PATENT DOCUMENTS

| | | | |
|---|---|---|---|
| 2,676,138 | 4/1954 | Hinkel | 435/188 |
| 3,594,325 | 7/1971 | Feierstein | 435/188 |
| 3,634,266 | 1/1972 | Theile | 252/132 |
| 3,637,509 | 1/1972 | Brennan | 252/99 |
| 3,650,961 | 3/1972 | Hudson | 252/99 |
| 3,661,786 | 5/1972 | Desforges | 252/99 |
| 3,676,352 | 7/1972 | Grimm | 252/99 |
| 3,687,853 | 8/1972 | Natali | 252/174.12 |
| 3,741,901 | 6/1973 | Ziffer | 435/188 |
| 3,944,497 | 3/1976 | Alterman | 252/96 |
| 4,381,247 | 4/1983 | Nakagawa | 252/95 |
| 4,391,725 | 7/1983 | Bossu | 252/90 |
| 4,403,994 | 9/1983 | Hignett | 8/111 |
| 4,417,994 | 11/1983 | Stoddart | 252/135 |
| 4,455,249 | 6/1984 | Broze | 252/95 |

*Primary Examiner*—Dennis Albrecht
*Attorney, Agent, or Firm*—Leonard Williamson; Richard C. Witte

[57] ABSTRACT

This invention relates to an enzyme and peroxyacid bleach granular composition comprising (1) a homogeneously mixed granulate of enzymes and alkaline buffer salt to protect the enzymes from deactivation when mixed with (2) a strong peroxyacid bleach granulate. This composition can also contain detergent surface-active agents, water-soluble builder salts, and other ingredients commonly used in detergents and laundry additive products.

21 Claims, No Drawings

DRY BLEACH AND STABLE ENZYME GRANULAR COMPOSITION

This is a continuation of application Ser. No. 750,569, filed June 28, 1985, now abandoned.

BACKGROUND OF THE INVENTION

This invention relates to an improved dry bleach and stable enzyme granular compositions.

During the last score of years the use of enzymes, especially of microbial origin, has been more and more common. Enzymes are used in, for example, the starch industry to produce glucose and fructose by means of amylases, amylglucosidases and glucose isomerases. In the dairy industry a vast tonnage of rennets is used and in the detergent industry proteases are normally used as additives in the washing powders to impart a better action on proteinaceous stains on the laundry.

On July 7, 1970, C. B. McCarty was granted U.S. Pat. No. 3,519,570 for enzyme-containing detergent compositions and a process for conglutination of enzymes and detergents. U.S. Pat. No. 3,784,476, van Kampen et al., issued Jan. 8, 1974, discloses a particulate enzyme-containing detergent composition containing a detergent surface-active agent, a water-soluble builder salt and discrete, shaped inorganic solids containing proteolytic or amylolytic enzymes. It should be noted that this patent does not teach an enzyme granulate with alkaline buffer salt as defined herein (pH of 7-11) used in combination with a peroxyacid bleach as disclosed herein.

U.S. Pat. No. 4,106,991, Markensen et al., issued Aug. 15, 1978, incorporated herein in its entirety, discloses an improved formation for enzyme granulates comprising enzyme, inorganic salts, a granulation binder, and finely divided cellulose fibers as 2-40% by weight of the granulate. Optionally, a waxy substance can be employed for the granulating agent, or to coat the granulate.

The granulates so produced are reported by Markensen et al. to have a higher physical stability and a higher resistance against abrasion than granulates without cellulose fibers and, consequently, a very low dust level. Markensen et al. does not disclose that use of alkaline buffer salts would improve the enzyme stability in the presence of peroxyacid bleach.

After the development of the granulated and coated enzymes presently offered to the detergent industry, the use of the enzymes in detergents has grown steadily.

Making a storage stable mixture of enzyme containing granulates and dry peroxyacid bleach granulates is a difficult task. In spite of the fact that some commercially available enzyme granulates are advertised as "perborate bleach stable," they are weak storagewise in the presence of strong peroxyacid bleach granulates. It should be noted that peroxyacid bleach granulates are relatively newcomers to the dry commercial laundry detergent and bleach markets. The term "bleach" as used herein unless otherwise specified means peroxyacid bleach and the terms "peroxyacid bleach powder" and "peroxyacid bleach granulates" are synonymous unless otherwise specified. The term "enzyme" as used hereinafter means raw enzyme, unless otherwise specified. The term "enzyme powder" means a mixture os raw enzyme and inorganic salts.

SUMMARY OF THE INVENTION

This invention relates to an improved dry bleach and stable enzyme granular composition. The enzyme granulate comprises a homogeneous mixture of proteolytic or amylolytic enzyme and alkaline buffer salt. The improved enzyme granulate is stable when mixed with peroxyacid bleach granulates.

OBJECTS

It is an object of the present invention to provide a dry bleach and stable enzyme granular composition. Other objects will become apparent in the light of this disclosure.

DETAILED DESCRIPTION OF THE INVENTION

This invention relates to an improved dry bleach and stable enzyme granular composition. The enzyme granulate comprises a homogeneous mixture of proteolytic or amylolytic enzyme and alkaline buffer salt. The improved enzyme granulate is stable when mixed with peroxyacid bleach granulates. The term "granular" as used herein means the composition comprising: (1) enzyme granulates and (2) peroxyacid bleach granulates, unless otherwise specified.

This invention has an improved water-soluble enzyme granulate containing enzymes, fillers and/or binders and an effective amount of alkaline buffer salt to protect the enzyme from deactivation via contact with peroxyacid bleach granulate. The alkaline buffer salt has a pH of from about 7 to about 11. The practical level of alkali buffer salt material contained in the granulate is from about 3% to about 97.5% by weight of the enzyme granulate. An alkaline buffer salt material as used herein is defined as a material having an effective amount of alkaline buffer salt and compatible inorganic salts. Some practical ratio levels of raw (proteolytic and/or amylase) enzyme to alkaline buffer salt material are from 1:4 to 1:200, preferably 1:6 to 1:100, and more preferably 1:20 to 1:50.

The improved enzyme granulate on a weight percentage basis preferably comprises:

TABLE 1

| | Enzyme Granulate Levels (%) | | |
|---|---|---|---|
| Ingredient | Preferred | Low | High |
| Proteolytic Enzyme | 4 | 0.5 | 15 |
| Amylase Enzyme | 1 | 0 | 5 |
| Alkaline Buffer Salt Material | 45 | 3.0 | 97.5 |
| Cellulose Filler & Binder | 25 | 2.0 | 40 |
| Optional Waxy Coating | 25 | 0 | 57 |

The weight percentages used herein refer to the weight of the granulate being discussed, unless otherwise specified.

The improved enzyme granulate preferably is made with a raw enzyme level of from about 0.5% to about 20% (0.25 to 10 Au/gram), and more preferably from about 1% to about 10% (0.5 to 5 Au/gram) by weight of the total composition. Au equals Anson units and is a term commonly used in the trade to describe enzyme activity. The filler and binder in the enzyme granulate can have a ratio of from 10:1 to 1:1. A practical level of cellulosic fillers in the total composition can be from about 2% to about 36%.

The stability of the alkaline buffer salt material/enzyme granulate of this invention is further improved with the inclusion of an antioxidant salt to the granulate. The antioxidant is preferably used at a level of from 1% to 40%, more preferably 2% to 30%. The enzyme granulate of this invention is further improved if it has a coating of alkaline buffer salt material including antioxidant with an overcoat of water-soluble nonionic waxy material over said coating. A coating level of at least 10% alkaline buffer salt material by weight of the enzyme granulate is preferred. The waxy overcoat is preferably used at a level of 10% to 30% and more preferably 15% to 25% by weight of said granulate.

Granular Compositions

The improved granular composition of this invention is a mixture of peroxyacid bleach granulates, improved enzyme granulates and, optionally, other laundry active powders including softeners, detergents, etc. Examples of powdered detergent materials are disclosed in U.S. Pat. No. 4,404,128, B. J. Anderson, issued Sept. 13, 1983, incorporated herein by reference. Examples of detergent composition and builder salts are disclosed in U.S. Pat. No. 3,784,476, van Kampen et al., issued Jan. 8, 1974, incorporated herein by reference. Examples of powdered peroxyacid bleach granulates are disclosed in U.S. Pat. No. 4,473,507, F. P. Bossu, issued Sept. 25, 1984, incorporated herein by reference. Suitable granular compositions can be formulated within the following ranges:

TABLE 2

| Ingredient | Weight % |
|---|---|
| Bleach granulate | 0.5-98 |
| Enzyme Granulate | 0.1-15 |
| Brightener | 0-3 |
| Alkali metal builder salts* | 0-80 |
| Anionic surfactant | 2-30 |
| Nononic surfactant | 1-10 |
| Ammonium and sodium sulfate | 0-80 |
| Perfume | 0-1 |
| Other laundry ingredients/ additives, i.e., softeners | 0-20 |

*Orthophosphates, pyrophosphates, tripolyphosphates, nitrilotriacetates, ethylenediamine tetraacetates, carbonates and silicates.

A preferred mixture is an enzyme-peroxyacid bleach granular composition comprising the alkaline buffer salt protected enzyme granulate of this invention and a peroxyacid bleach granulate having a weight ratio of from 1:1 to 1:1500 of enzyme granulate to bleach granulate, preferably 1:3 to 1:30. Details of such a preferred mixture is disclosed below.

The Alkaline Buffer Salt Material

The term "alkaline buffer salt material" as used herein means a salt having a pH of 7-11 and which provides a comparable pH for the enzyme granulate in the presence of acidic substances for an extended period of time. Thus, the alkaline buffer salt material useful in the present invention can include any one of a number of suitable compatible inorganic salts which have a pH of about 7-11. A pH of 8-10 is preferred. The pH of a salt is measured as a 10% solution of the salt. Some preferred alkaline buffer salts are potassium bicarbonate, potassium carbonate, tetrapotassium pyrophosphate, potassium tripolyphosphate, sodium bicarbonate and sodium carbonate. Other suitable alkaline buffer salts can be used.

The alkaline buffer salt material can constitute 97.5% of the solids in the enzyme granulate. In this case at least 2% is cellulosic fibers and 0.5% enzyme per Table 1. However, other compatible materials can be included as part of the alkaline buffer salt material, e.g., other inorganic salts, fillers, binders, etc. Calcium is a preferred component and can be added as calcium sulfate or calcium chloride.

The Antioxidant

As used herein the term "antioxidant" means a substance that opposes oxidation or inhibits reaction provided by oxygen or peroxides. The antioxidant is an enzyme stability booster for the alkaline buffer salt enzyme granulate. The antioxidant increases the stability of the enzyme when used in conjunction with alkaline buffer salt. The preferred enzyme granulate can contain an antioxidant salt, preferably at a level of from 1-40%, and more preferably 2-30% by weight of the enzyme granulate. Some preferred antioxidant salts are sodium sulfite, sodium bisulfite and sodium thiosulfate. Other suitable antioxidant salts can be used.

The Enzyme Granulate

The enzyme granulate of the present invention has a particle size of from 100 to 1600μ, preferably from about 200 to about 800μ, more preferably 300-500.

A preferred process for making enzyme granulates of this invention comprises drum granulating an enzyme material, inorganic salts, a granulation binder, a liquid phase granulating agent, and finely divided cellulose fibers. In accordance with the present invention the inorganic salts are selected to include an effective amount of alkaline buffer salt material to protect the enzyme from rapid deactivation upon exposure to peroxyacid bleach granulates.

The process for the production of enzyme granulates comprises the introduction into a drum granulator of from 2 to 40% by weight of cellulose in fibrous form, from 0 to 10% by weight of a binder as herein defined, 0.5% to 20% enzyme and 3% to 97.5% alkaline buffer salt material in an amount which generates the intended enzyme activity in the finished granulate, a liquid phase granulating agent consisting of a waxy substance, as defined herein, and/or water, in an amount of between 5 and 70% by weight, whereby the maximum amount of waxy substance is 40% by weight and the maximum amount of water is 70% by weight, whereby all percentages are referring to the total amount of dry substances, the sequence of the introduction of the different materials being arbitrary, except that at least a major part of the granulating agent is introduced after at least a substantial part of the dry substances is introduced in the granulator, whereafter the granulate, if necessary, is dried in a conventional manner, preferably in a fluid bed.

The cellulose in fibrous form can be sawdust, pure, fibrous cellulose, cotton, or other forms of pure or impure fibrous cellulose. Several brands of cellulose in fibrous form are on the market, e.g., CEPO and ARBOCEL. In a publication from Svenska Tramjolsfabrikerna AB, "Cepo Cellulose Powder," it is stated that for Cepo S/20 cellulose the approximate minimum fiber length is 500μ, the approximate average fiber length is 160μ, the approximate maximum fiber width is 50μ and the approximate average fiber width is 30μ. Also, it is stated that CEPO SS/200 cellulose has an approximate maximum fiber length of 150μ, an approximate average fiber length of 50μ, an approximate maximum fiber width of 45μ and an approximate average fiber width of 25μ. Cellulose fibers with these dimensions are very well suited for the purpose of the invention.

The binders used in the process are the binders conventionally used in the field of granulation with a high melting point or with no melting point at all and of a nonwaxy nature, e.g., polyvinyl pyrrolidone, dextrina, polyvinylalcohol, and cellulose derivatives, including for example hydroxypropyl cellulose, methyl cellulose or CMC. A granulate cannot be formed on the basis of cellulose, filler, enzyme, alkaline buffer salt material and a binder, without the use of a granulating agent, as defined below.

The term "enzyme" as used herein means raw enzyme unless otherwise specified. The term "enzyme powder" means raw enzyme mixed with inorganic salts such as NaCl, $CaCl_2$, etc. All enzymes can be granulated by means of said process. Preferably, amylases and proteinases are granulated according to the invention. Specific examples are ALCALASE (a *Bacillus licheniformis* proteinase), ESPERASE and SAVINASE (microbial alcaline proteinases produced according to British Pat. No. 1,243,784) and TERMAMAYL (a *Baccilus licheniformis* amylase). The enzyme can be introduced into the granulator as a predried milled powder or as a solution, for example, a concentrated enzyme solution prepared by ultrafiltration, reverse osmosis or evaporation.

The granulating agent is water and/or a waxy substance. The granulating agent is always used as a liquid phase in the granulation process; the waxy substance if present therefore is either dissolved or dispersed in the water or melted. By a "waxy substance" is understood a "wax" which possesses all of the following characteristics: (1) the melting point is between 30° and 100° C., preferably between 40° and 60° C., (2) the substance is of a tough and not brittle nature, and (3) the substance possesses substantial plasticity at room temperature.

Both water and waxy substance are granulating agents, i.e., they are both active during the formation of the granulate; the waxy substance stays as a constituent in the finished granulate, whereas the majority of the water is removed during the drying. Thus, in order to refer all amounts to the finished, dry granulate, all percentages are calculated on the basis of total dry granulate unless otherwise specified, which means that water, one of the granulating agents, is not added to the other constituents when calculating the percentage of water, whereas the waxy substance, the other granulating agent, has to be added to the other dry constituents when calculating the percentage of waxy substance. Examples of waxy substances are polyglycols, fatty alcohols, ethoxylated fatty alcohols, higher fatty acids, mono-, di- and triglycerolesters of higher fatty acids, e.g., glycerol monostearate, alkylarylethoxylates, and coconut monoethaneolamide.

An illustrative summary of a process used to make an enzyme granulate is:

1. Provide dry enzyme powder, cellulose fillers, alkaline buffer salt materials, binders, etc.
2. Mix the dry powders of the granulate.
3. Wet the powder mixture with granulating agent, e.g., water or waxy melt.
4. Process the wet powder mixture of Step 3 in a granulating apparatus (rotating knife) until the granulate has the desired particle size distribution.

A cylindrical Lodige type mixer FM 130 DIZ (U.S. Pat. No. 3,027,102) can be used in the process for this step. The mixer is equipped with both plough shaped mixers mounted on a horizontal (axial) rotating shaft and a granulating device, consisting of one or more cross knives mounted on a shaft introduced into the mixer through the cylindrical wall in a direction perpendicular to the abovementioned horizontal rotating shaft (i.e., radial of the cylinder).

5. Dry in a fluidized bed the moist granulate of Step 4 until a dryness which satisfies both the requirements of enzyme stability and the requirements of free-flowing properties and mechanical strength. Usually this will correspond to a water content less than 10%, preferably less than 3% and more preferably bone dry. In the instances where the granulating agent is exclusively or principally a waxy substance only cooling may be required.
6. Optionally coating the enzyme granulate with an alkaline buffer salt coating, a waxy or some other compatible substance.

Optional Alkaline Buffer Salt Coating of the Enzyme Granulate

The enzyme granulate produced in the present invention can also be coated with alkaline buffer salt using any number of known apparatuses. Coating in a fluidized bed is preferred. Examples of suitable apparatuses and processes are disclosed in U.S. Pat. No. 3,196,827, Wurster and Lindlof, issued July 27, 1965; U.S. Pat. No. 3,253,944, Wurster, issued May 31, 1966; and U.S. Pat. No. 3,117,027, Lindlof and Wurster, issued Jan. 7, 1964, all incorporated herein by reference.

U.S. Pat. No. 3,117,027 discloses a preferred fluidized bed apparatus which can be used for coating the enzyme granulates produced in the present invention. The fluidized bed will provide substantially uniformly enzyme coated granulates.

The coating process of the present invention comprises:

1. Forming an enzyme granulate having a particle size of from 100 to 1600μ, preferably 200 to 800μ, with or without optional waxy coating.
2. Coating the enzyme granulate with an effective amount of alkaline buffer salt material, preferably at a level of from about 10% to about 100% by weight of the enzyme granulate on a dry weight basis. The enzyme granulate should be surrounded by the coating and the coating should contain an effective amount of alkaline buffer salt.

The protective coating is preferably applied to the enzyme granulate as a 15% to 70% (preferably 20% to 50%) solids aqueous solution in a fluidized bed. The temperature range of the solution can be about 60°-82° C. (140°-180° F.), and is preferably about 65°-77° C. (150°-170° F.). The air temperature of the fluidized bed is 45° to 77° C. for the coating/drying operation. The rate of addition of the coating solution and the rate of drying are dependent on the solution concentration, temperature of air, volume, etc.

Calcium Present in Granulate and Coating

The enzyme granulate of this invention can be improved if it contains from about 40 to 3000 ppm of calcium calculated as calcium chloride. Calcium can be added to the granulate as calcium chloride or calcium sulfate powder in the granulation process or by using water containing a calcium content of 100-500 ppm, preferably 170-300 ppm, calculated as calcium chloride in the water used in the granulation and/or coating process.

Optional Waxy Coating Material

A nonionic waxy material can be applied over the enzyme granulate or over the alkaline buffer salt coated enzyme granulate. The practical levels of optional waxy coating material is up to 57% by weight of the composition, preferably 5–30%. Examples of such waxy coatings are polyethylene glycols, fatty alcohols, ethoxylated fatty alcohols, higher fatty acids, mono-, di- and triglycerolesters of fatty acids, e.g., glycerol monostearate, alkylarylethoxylates and coconut monoethanolamide. Preferred nonionic waxy substances are $TAE_{22}$ (tallow alcohol condensed with 22 moles of ethylene oxide per mole of alcohol), PEG 1500–8000 (polyethylene glycol of molecular weight 1500–8000) and palmitic acid. Other waxy coatings having a melting point of at least 38° C., preferably at least 50° C., can also be used. For example, this waxy coating is melted (50°–70° C.) and is sprayed onto the granulate in a fluidized bed where cool air (15°–30° C.) is applied to solidify the waxy coating.

EXAMPLE I

A preferred enzyme granulate can be made using the procedure outlined above using the following ingredients:

| Ingredient | Wt % |
|---|---|
| Proteolytic Enzyme | 4 |
| Amylase Enzyme | 1 |
| Alkaline Buffer Salt Material[1] | 45 |
| Cellulose Filler[2] | 20 |
| Binder[3] (polyvinyl pyrrolidone) | 5 |
| Waxy Overcoat (PEG 1500) | 25 |

[1] 20% $KHCO_3$, 5% $Na_2SO_3$, 20% $CaCl_2$/NaCl
[2] Cellulose Powder - CEPO S20
[3] Selected from polyvinyl pyrroildone, dextrin, polyvinyl alcohols and cellulose derivatives.

EXAMPLE II

A 6 inch Wurster Fluidized Bed Coating Unit with a capacity of about 1 liter can be used. The enzyme granulate of Example I can be optionally coated as follows: 800 grams of enzyme granulate are added to the fluid bed dryer. To this a 1,000 gram 70° C. aqueous solution, containing 200 grams of potassium bicarbonate and 40 grams of sodium sulfite, is sprayed on. The coated enzyme granulate is then dried at a fluid bed temperature of 75° C. to contain less than 0.5% water. The coated enzyme granulate is then removed from the fluid bed dryer and weighed to confirm coating level.

About 800 grams of the alkaline buffer salt/antioxidant salt-coated enzyme granulate is then placed back into the fluid bed dryer. To this 200 grams of $TAE_{22}$ are sprayed on at 55° C. and allowed to cool in the dryer with air temperature 20° C.

| Final weight %: | | |
|---|---|---|
| Enzyme Granulate | | 61.54% |
| Protective Coating: | | |
| Potassium Bicarbonate | 15.38 | 18.46 |
| Sodium Sulfite | 3.08 | |
| $TAE_{22}$ Overcoating | | 20.00 |
| Total | | 100.00 |

The ratio of enzyme granulate to protective coating is about 3.3 to 1. The pH of the coating is 8.5.

EXAMPLE III

The enzyme granulates similar to that described in Examples I or II are dry mixed with peroxyacid bleach granulates.

| | Wt % | Grams |
|---|---|---|
| Peroxyacid Bleach Granulate | | |
| Diperoxydodecanedioic Acid | 20.75 | |
| Dodecanedioic Acid | 1.85 | |
| Boric Acid | 22.75 | |
| $Na_2SO_4$ | 28.06 | |
| Sodium Acid Pyrophosphate | 5.00 | |
| $C_{13}$LAS | 4.50 | |
| Enzyme Granulate of Example I or II* | 83 | 20 |
| | 17 | 4 |
| | 100 | 24 |

*2.0 Au/gram protease activity.

The process used to make the peroxyacid bleach granulate in Example III is disclosed in U.S. Pat. No. 4,497,757, Beimesch and Hortel, issued Feb. 2, 1985, incorporated herein by reference in its entirety.

EXAMPLE IV

A detergent powder containing the following components:

| | Weight % |
|---|---|
| Diperoxydodecanedioic acid bleach granulate (Ex. III) | 25 |
| Enzyme granulates of Example I or II | 2 |
| Sodium salt of straight chain $C_{12}$ alkylbenzene sulfonate | 20 |
| Sodium tripolyphosphate | 35 |
| Sodium sulfate | 12 |
| Sodium silicate | 4 |
| Brightener | 1 |
| Perfume capsules | 0.3 |
| Water, perfume | Balance |

EXAMPLE V

A laundry additive containing the following components:

| | Weight % |
|---|---|
| Diperoxydodecanedioic acid bleach granulate* | 90.2 |
| Enzyme granulates of Example I or II | 2 |
| Brightener and sodium silicate | 7 |
| Perfume capsules | 0.3 |
| Water | Balance |

*The peroxyacid bleach granulate of Example III is cut with sodium sulfate to adust peroxyacid level to about 8% of the bleach granulate.

This invention offers an improved storage stable granular composition comprising an enzyme granulate which is storage stable with a peroxyacid bleach granulate, enabling them to be used together in a detergent or laundry additive product for combined bleaching and stain removal performance.

What is claimed is:

1. A storage stable granular composition comprising:

(I) a low dust enzyme granulate including a homogeneous mixture of 0.5% to 20% raw enzyme selected from amylases and proteases and mixtures thereof, 3% to 97.5% alkaline buffer salt material selected from the group consisting of potassium bicarbonate, potassium carbonate, sodium bicarbonate, and mixtures thereof, an antioxidant inorganic salt selected from the group consisting of sodium sulfite, sodium bisulfite, sodium thiosulfate, and mixtures thereof, 2% to 40% cellulosic filler and binder, with said raw enzyme having an activity of about 0.25–10 Au/gram, said binder selected from nonwaxy polyvinyl pyrrolidone, dextrina, polyvinylalcohol, cellulose derivatives, and mixtures thereof; and (II) a peroxyacid bleach granulate, wherein said (I) and (II) have a weight ratio of from about 1:1 to about 1:1500;

wherein said alkaline buffer salt material has a pH of above 7 to about 11;

wherein said raw enzyme and said alkaline buffer salt material have a weight ratio of from 1:4 to 1:200;

wherein said cellulosic filler and binder of said (I) have a weight ratio of about 1:1 to 10:1;

wherein said enzyme granulate (I) is made with a granulating agent selected from a waxy substance and water, said waxy substance having a melting point of from about 30° C. to about 100° C., said granulating agent being used at a level of from about 5% to about 70% by weight of dry substances, and wherein a maximum of waxy substance used is 40%.

2. The granular composition of claim 1 wherein said antioxidant to alkaline buffer salt have a weight ratio of from 10:1 to 1:50.

3. The granular composition of claim 1 or 2 wherein said (I) and said (II) have a weight ratio of 1:3 to 1:30 and said pH is 8 to 10 and said raw enzyme and said alkaline buffer salt material have a weight ratio of 1:6 to 1:100.

4. The granular composition of claim 1 or 2 wherein said raw enzyme and said alkaline buffer salt material have a weight ratio of 1:20 to 1:50.

5. The granular composition of claim 1 or 2 wherein antioxidant is present at a level of 1% to 40% by weight of said enzyme granulate and said alkaline buffer salt is present at an effective level to stabilize said enzyme from rapid deactivation in the presence of peroxyacid bleach granulate.

6. The granular composition of claim 5 wherein said antioxidant is present at a level of 2% to 30% by weight of said enzyme granulate.

7. The granular composition of claim 1 or 2 wherein said enzyme granulate contains calcium ion selected from calcium sulfate or calcium chloride at a level of 40 to 3000 ppm by weight of said enzyme granulate.

8. The granular composition of claim 1 or 2 wherein said enzyme granulate is surrounded with a coating of water-soluble nonionic wax having a melting point of at least about 38° C.

9. The granular composition of claim 8 wherein said nonionic wax is selected from the group consisting of: fatty alcohols, polyethylene glycols, ethoxylated fatty alcohols, higher fatty acids, mono-, di- and triglycerolesters of fatty acids, e.g., glycerol monostearate, alkylarylethoxylates and coconut monoethanolamide, and mixtures thereof.

10. The granular composition of claim 9 wherein said nonionic wax is selected from the group consisting of: tallow alcohol condensed with 22 moles of ethylene oxide per mole of alcohol, polyethylene glycol of molecular weight 1500–8000 and palmitic acids.

11. The granular composition of claim 1 or 2 wherein said enzyme granulate includes a nonionic waxy coating at a level of from about 5% to about 57% by weight of said enzyme granulate, and has a melting point of at least 50° C.

12. The granular composition of claim 11 wherein said coating of said water-soluble nonionic waxy coating is present at a level of 10% to 30% by weight of said enzyme granulate.

13. The granular composition of claim 11 wherein said water-soluble nonionic waxy coating is present at a level of 15% to 25% by weight of said enzyme granulate.

14. The granular composition of claim 1 or 2 wherein said enzyme granulate is coated with a protective coating containing an effective amount of additional alkaline buffer salt material having a pH of from above 7 to 11; said protective coating surrounding said enzyme granulate and providing improved enzyme stability in the presence of said peroxyacid bleach granulate.

15. The granular composition of claim 14 wherein said protective coating is from about 10% to about 67% by weight of said coated enzyme granulate.

16. The granular composition of claim 14 wherein said protective coating surrounding said enzyme granulate is from about 50% to about 80% by weight of said coated enzyme granulate.

17. The granular composition of claim 14 wherein said protective coating contains 50% to 100% alkaline buffer salt by weight of said protective coating.

18. The granular composition of claims 14 wherein said protective coating contains 50–100% alkaline buffer salt by weight of said protective coating, and wherein when said alkaline buffer salt is present at a level of from about 5% to about 10% by weight of said enzyme granulate, and wherein the balance of said protective coating is selected from antioxidants, calcium chloride and other compatible inorganic salts.

19. The granular composition of claim 14 wherein said alkaline buffer salt material protective coating having a pH of 8–10, said enzyme granulate to said protective coating has a ratio of from 4:1 to 1:1.

20. The granular composition of claim 14 wherein said protective coating is a mixture of alkaline buffer salt and antioxidant, said coating having a pH of 8 to 10.

21. The granular composition of claim 14 wherein said coating alkaline buffer salt is selected from the group consisting of potassium bicarbonate, potassium carbonate, tetrapotassium pyrophosphate, tripotassium polyphosphate, sodium bicarbonate and sodium carbonate, and mixtures thereof, said alkaline buffer salt in said protective coating is present at a level of 5% to 50% by weight of said enzyme granulate.

* * * * *